United States Patent [19]

Lindner

[11] Patent Number: 5,480,898
[45] Date of Patent: Jan. 2, 1996

[54] STORAGE-STABLE AQUEOUS SOLUTIONS OF ISOTHIAZOLIN-3-ONES

[75] Inventor: Wolfgang Lindner, Seelze, Germany

[73] Assignee: Riedel-de Haen Aktiengesellschaft, Seelze, Germany

[21] Appl. No.: 334,959

[22] Filed: Nov. 7, 1994

[30] Foreign Application Priority Data

Nov. 18, 1993 [DE] Germany .......................... 43 39 248.2

[51] Int. Cl.⁶ .......................... A01N 43/80; C07D 275/03
[52] U.S. Cl. .............................................. 514/372; 548/213
[58] Field of Search .............................. 514/372; 548/213

[56] References Cited

U.S. PATENT DOCUMENTS

| | | | |
|---|---|---|---|
| 3,870,795 | 3/1975 | Miller et al. ............... | 424/270 |
| 4,067,878 | 1/1978 | Miller et al. ............... | 260/302 A |
| 4,490,462 | 12/1984 | Kawaguchi et al. ....... | 548/213 |
| 5,153,213 | 10/1992 | Schmidt ..................... | 514/372 |
| 5,286,871 | 2/1994 | Schmidt ..................... | 548/213 |
| 5,356,952 | 10/1994 | Schmidt ..................... | 523/122 |
| 5,376,695 | 12/1994 | Schmidt ..................... | 523/122 |

FOREIGN PATENT DOCUMENTS 0436744  7/1991  European Pat. Off. .

*Primary Examiner*—Allen J. Robinson
*Attorney, Agent, or Firm*—Connolly and Hutz

[57] ABSTRACT

The present invention relates to a storage-stable aqueous solution of one or more compounds of the general formula I

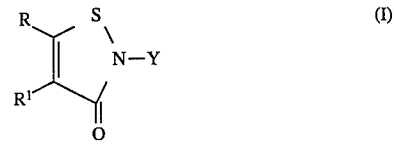

wherein Y, R and $R^1$ are as defined in claim 1, which comprises a noble metal ion.

16 Claims, No Drawings

STORAGE-STABLE AQUEOUS SOLUTIONS OF ISOTHIAZOLIN-3-ONES

The present invention relates to storage-stable aqueous solutions of isothiazolin-3-ones which comprise a noble metal ion.

Isothiazolin-3-ones are microbicidally active substances which can be added to aqueous industrial materials such as, for example, dispersions, emulsion paints, adhesives, gelatine, sizes based on native substances, surfactant solutions, or functional liquids such as drilling muds and metalworking fluids, for protection from microorganisms (bacteria, moulds, yeasts, algae). In this context they combine high microbiological activity, easy degradability in the environment and easy meterability. Preservatives based on isothiazolin-3-ones are employed by the end user in the form of dilute formulations in which water is to be employed as the diluent.

However, Isothiazolin-3-ones are relatively unstable in aqueous solution and are readily inactivated by decomposition. Accordingly, several methods are already known for stabilizing such solutions. Thus, for example, Ep-A 436 744 proposes the use of oxidizing agents, in particular hydrogen peroxide and sodium perborate, in amounts of 0.1 to 3% by weight, based on the total solution. Disadvantages of this are the intrinsic relative instability of, for example, hydrogen peroxide and the diverse possible reactions with the systems to be treated, at least in the amounts required. Thus, in particular, oxidizing agents cannot be employed in the amounts mentioned for preserving materials for the photographic industry, such as, for example, gelatine, photographic emulsions, developer baths and the like. Isothiazolinones furthermore are oxidized on the sulphur by peroxides and form products of unknown toxicity.

It is known from U.S. Pat. No. 3,870,795 to use metal nitrates or nitrites, for example also silver nitrate, in amounts of 1 to 30% by weight, based on the total solution, for stabilization. According to this document, metal salts other than nitrates and nitrites are ineffective. Disadvantages of the use of nitrates or nitrites are the possible formation of toxic nitrosamines and the risk that constituents of the formulation will be nitrosated.

The use of high salt contents in, for example, wax emulsions of plastics dispersions and products prepared therefrom, such as paints, adhesives or synthetic resin plasters, furthermore leads to incompatibilities, such as coagulation or the formation of inhomogeneities.

There is therefore the need for a stabilization method which does not have the disadvantages described, is widely applicable and is particularly suitable for materials of the photographic industry.

It has now been found, surprisingly, that the object can be achieved by small amounts of noble metal ions.

The present invention thus relates to a storage-stable aqueous solution of one or more isothiazolin-3-ones of the general formula I

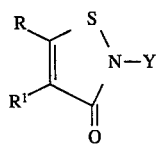

wherein

Y is hydrogen, $(C_1-C_8)$-alkyl, $(C_2-C_{18})$-alkenyl, $(C_3-C_{12})$-cycloalkyl or $(C_6-C_{10})$-aryl, and R and $R^1$ independently of one another are hydrogen, halogen, $(C_1-C_4)$-alkyl or $C_4$-alkenyl or, together with the carbon atoms carrying them, form a 3- to 6-membered carbon ring which contains 1, 2 or 3 double bonds; characterized in that it comprises a noble metal ion in an amount of up to 1 g/kg of compound of the general formula I. $(C_1-C_8)$-alkyl standing for Y and $(C_1-C_4)$-alkyl standing for R or $R^1$ can be straight-chain or branched and can be, for example, methyl, ethyl, n-propyl, i-propyl, n-butyl, i-butyl, tert-butyl or sec-butyl. $(C_1-C_8)$-Alkyl can also additionally be, for example, n-pentyl, n-hexyl, n-heptyl or n-octyl.

$(C_2-C_{18})$-alkenyl radicals can also be straight-chain or branched and are, in particular, vinyl or allyl. $(C_3-C_{12})$-Cycloalkyl radicals are, in particular, cyclopentyl, cyclohexyl and cyclooctyl.

$(C_6-C_{10})$-aryl is, in particular, phenyl.

Halogen is, in particular, fluorine, chlorine or bromine. The carbon ring formed by R and $R^1$ together with the carbon atoms carrying them is preferably five-membered. Particularly preferably, it is five-membered and contains a double bond, i.e. is a fused-on cyclopentenyl ring.

Y is preferably hydrogen or $(C_1-C_8)$-alkyl, and particularly preferably methyl.

R and $R^1$ preferably independently of one another are hydrogen or halogen. Particularly preferably, R is chlorine and $R^1$ is hydrogen.

Noble metal ions in the context of the present invention are understood as meaning, in particular, ions of ruthenium, thodium, palladium, osmium, iridium, platinum, silver and gold. Silver ions, gold ions and palladium ions are preferred. The solutions according to the invention comprise the noble metal ions in amounts of up to 1 g/kg of compound of the general formula I, usually in amounts of 0.01 mg to 1 g/kg of compound of the general formula I. Particularly preferred amounts are 10 mg to 200 mg/kg of compound of the general formula I.

It is of course to be remembered here that the upper limit is determined by the solubility of the noble metal salt employed. For example, however, in the case of $Ag^*$, concentrations which are far below the solubility products of the sparingly soluble silver halides are sufficient.

The noble metal ions are preferably introduced into the solutions according to the invention in the form of their salts. The nature of the anion is not critical here, as long as the solubility of the salt is sufficient to achieve the necessary noble metal ion concentration. Suitable anions are, for example, chloride, perchlorate, bromide, iodide, nitrate, sulphate, acetate, citrate, ascorbate, maleate, oxalate, methylsulphonate, carbonate and phosphate.

The solutions according to the invention comprise the compounds of the general formula I as a rule in amounts of 0.1 to 50% by weight, based on the total solution. A content of 0.5 to 10% by weight is preferred. Here also, the upper limit is determined by the solubility of the compounds of the general formula I.

The content of noble metal ions in the solutions according to the invention, based on the total solution, is thus, for example, 0.05% by weight for a 50% by weight content of compound of the general formula I and an amount used of 1 g/kg.

The compounds of the general formula I can be employed as such or else in the form of their known metal salt complexes. The latter are described, for example, in EP-A 436744 and U.S. Pat. No. 3,870,795.

The aqueous solutions according to the invention can comprise one or more of the compounds of the general formula I. If they comprise two or more, the mixing ratios thereof with respect to one another are not at all critical. The ratio of two compounds of the general formula I is preferably 1:(0.1 to 50), particularly preferably 1:(1 to 15).

A particularly preferred aqueous solution according to the invention comprises 5-chloro-2-methylisothiazolin-3-one and 2-methylisothiazolin-3-one in a ratio of (1 to 10):1, in particular (2 to 4):1.

In addition to the noble metal ions or salts, the aqueous solutions according to the invention may also include other soluble metal salts as a result of their production or for other reasons. Examples of cations which may be present here are lithium, sodium, potassium, calcium, barium, aluminium, iron, manganese, nickel, cobalt, tin or zinc ions. Possible anions are chloride, perchlorate, bromide, iodide, nitrate, sulphate, acetate, citrate, ascorbate, maleate, oxalate, methylsulphonate, carbonate and phosphate.

The addition to water, the aqueous solutions according to the invention can also additionally comprise water-miscible organic solvents. Suitable water-miscible organic solvents are, for example, alcohols, such as methanol, ethanol, n-propanol, i-propanol and tert-butanol, ketones, such as acetone and methyl ethyl ketone, ethers, such as methoxybutanol, and also glycols, as well as di- and polyglycols and ethers and esters thereof.

These organic solvents can be present in amounts of 1 to 50% by weight, based on the total solution. Finally, the solutions according to the invention can also additionally comprise other compatible active compounds with which the microbicidal effectiveness of the compounds of the general formula I can be increased. Suitable active compounds are, in particular, bronopol, chloroacetamide and aldehydes, such as, for example, formaldehyde, and the formaldehyde depot compounds prepared therefrom, which can be employed in amounts of 1 to 20% by weight, based on the total solution.

The aqueous solutions according to the invention are as a rule prepared by simply dissolving the components in water. Since the compounds of the general formula I are usually present in the form of hydrochlorides, as a result of their preparation, neutralization by means of metal hydroxides or ion exchangers must be carried out after they have been dissolved.

The compounds of the general formula I and their metal salt complexes are known and/or can be prepared by known methods. For example, however, concentrated mixtures of 5-chloro-2-methylisothiazolin- 3-one and 2-methylisothiazolin-3-one are also commercially available.

The aqueous solutions according to the invention are adequately stable and do not have the disadvantages of the prior art. They can be employed in all industrial systems in which microorganisms can grow, for example in plastics dispersions, emulsion paints, metalworking fluids and cooling circulations, in papermaking, in fuels and the like. The solutions according to the invention which have been stabilized with silver ions can be employed particularly advantageously in the photographic industry, such as, for example, in photographic emulsions, in baths used photographically and the like, where the addition of other metal salts is not possible. Their use in plastics dispersions which coagulate on addition of preservatives stabilized with polyvalent salts such as, for example, magnesium nitrate or calcium nitrate is just as particularly advantageous.

Microorganisms which can be combated particularly advantageously with the solutions according to the invention are bacteria such as, for example, *Bacillus subtilis, Enterobacter aerogenes, Escherichia coli, Proteus vulgaris, Pseudomonas aeruginosa* and *Pseudomonas fluorescens;* yeasts such as, for example, *Candida albicans* and *Saccharomyces cerevisiae;* moulds such as, for example, *Aspergillus niger, Chaetomium globosum, Penicillium funiculosum* and *Ulocladium consortiale;* and algae such as, for example, *Chlorella fusca* and *Anabaene cylindrica.*

EXAMPLE 1

Stabilized solutions were prepared from in each case 10 g of a commercially available mixture of 5-chloro-2-methylisothiazolin- 3-one (5CLMIT) and 2-methylisothiazolin-3-one (MIT) having a weight ratio of 5CLMIT:MIT of 8:1 and 90 g of deionized water (solution A:Ag content 5.3 mg/kg; solution B:Ag content 0.53 mg/kg). A pH of 4–5 was established with acetic acid and the solutions were stored at 40° C. in closed glass vessels. The stability was determined by the content of 5CLMIT, which was measured after 2, 4 and 15 weeks by means of HPLC (250 mm long RP-18 column of internal diameter 4 mm; packing Hypersil ODS 5μ; gradient elution with acetonitrile/water increasing linearly from the ratio 20:80 to 100:0; UV detection at 275 nm). A non-stabilized solution (solution C) and a solution stabilized with $Cu(NO_3)_2 \cdot 3H_2O$ in accordance with U.S. Pat. No. 3,870,795 (solution D) were used for comparison.

Results:

| Solution | Storage | Content of 5CLMIT | Loss of 5CLMIT | Appearance |
| --- | --- | --- | --- | --- |
| A | 0 | 1.12% | — | clear, colourless |
| 5.3 mg/kg | 2 weeks | 1.12% | 0% | " |
| of Ag | 4 weeks | 1.12% | 0% | " |
|  | 15 weeks | 1.12% | 0% | " |
| B | 0 | | 1.12% | -clear, colourless |
| 0.53 mg/kg | 2 weeks | 1.12% | 0% | " |
| of Ag | 4 weeks | 1.12% | 0% | " |
|  | 15 weeks | 1.08% | 4% | " |
| C | 0 | 1.12% | — | clear, colourless |
| no stabilizer | 2 weeks | 0.87% | 22% | cloudy |
|  | 4 weeks | 0.73% | 35% | cloudy, sediment |
|  | 15 weeks | 0% | 100% | " |
| D | 0 | | 1.14% | -clear, blue |
| 8030 mg/kg | 2 weeks | 1.14% | 0% | clear, blue |
| of Cu | 4 weeks | 1.13% | 1% | slightly cloudy |

EXAMPLE 2

Example 1 was repeated with $PdSO_4$ as the stabilizer (Pd content: 8.5 mg/kg). The original content of 5CLMIT of 1.14% was unchanged after two weeks and was 1.09% after 4 weeks (loss: 5%).

EXAMPLE 3

Solutions prepared according to Example 1 were stabilized with tetrachloroaurate (III) ($HAuCl_4$; normal solution of 0.1 g of Gold FIXANAL® from Riedel-de Haen AG, Seelze) and stored at 50° C.

Results

| Solution | Storage | Content of 5CLMIT | Loss of 5CLMIT |
| --- | --- | --- | --- |
| A | 0 | 1.24% | — |
| 5 mg/kg of Au | 1 week | 0.96% | 23% |
|  | 2 weeks | 0.85% | 31% |
| B | 0 | 1.24% | — |
| 0.5 mg/kg of Au | 1 week | 0.87% | 30% |
|  | 2 weeks | 0% | 68% |

-continued

| Solution | Storage | Content of 5CLMIT | Loss of 5CLMIT |
|---|---|---|---|
| C no stabilizer | 0 1 week | 1.24% 0% | — 100% |

EXAMPLE 4

A commercially available aqueous solution of 10% by weight of 5-chloro-2-methylisothiazolin-3-one (5CLMIT) and 3.6% strength by weight of 2-methylisothiazoline-3-one (MIT), which included 7% of magnesium chloride and 11% of magnesium nitrate as a result of its production, was diluted to a factor of 10 with deionized water. The solution was stabilized by addition of silver nitrate (solution A) and stored at 50° C. The content of 5CLMIT was monitored as described in Example 1. The solution without addition of $AgNO_3$ (solution 3) corresponds to the doctrine of U.S. Pat. No. 3,870,795.

| Solution | Storage | Content of 5CLMIT | Loss of 5CLMIT | Appearance |
|---|---|---|---|---|
| A | 0 | 1.02% | — | clear |
| 4.8 mg/kg of Ag | 2 weeks | 1.02% | 0% | " |
|  | 6 weeks | 1.02% | 0% | " |
| B | 0 | 1.04% | — | clear |
| Comparison | 2 weeks | 1.01% | 3% | " |
|  | 6 weeks | 0.97% | 7% | sediment |

EXAMPLE 5

If preservatives which comprise 5CLMIT and are stabilized with magnesium salts are used in plastics dispersions, a so-called electrolyte shock can occur, the polymer coagulating out of the dispersion and forming inhomogeneities or a sediment.

The following experiment was carried out in this context:

0.5 g of solution A according to Example 1 was stirred homogeneously with 100 g of a pure acrylate dispersion free from sieve residue. The dispersion was stored at 25° C. for 2 days, the sieve residue was then determined in accordance with DIN 53 786 on a wire sieve tray of mesh width 0.056 mm, the dispersion was stored for a further 3 days to 50° C. and, finally, the sieve analysis was repeated.

For comparison, 0.5 g of a solution according to U.S. Pat. No. 3,870,795 comprising 1.1% by weight of magnesium nitrate and 0.7% by weight of magnesium chloride and the same active compound content (solution B) was subjected to the same process.

| Solution | Amount of coarse-particled contents after | |
|---|---|---|
|  | 2 days | 5 days |
| A 5.3 mg/kg of Ag | 0 | 0 |
| B 1.1% of Mg $(NO_3)_2$ 0.7% of $MgCl_2$ | 0.21 g | 0.25 g |

I claim:

1. Storage-stable microbicidally active aqueous solution comprising from about 0.1 to about 50% by weight based on the total weight of the solution of one ore more isothiazolin-3-ones of formula I

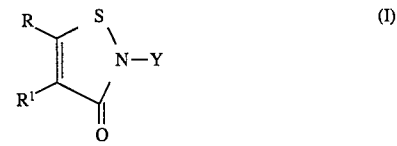

wherein

Y is hydrogen, $(C_1-C_8)$-alkyl, $(C_2-C_{18})$-alkenyl, $(C_3-C_{12})$-cycloalkyl or $(C_6-C_{10})$-aryl, and R and $R^1$ independently of one another are hydrogen, halogen, $(C_1-C_4)$-alkyl or $C_4$-alkenyl, or, together with the carbon atoms carrying the, form a 3- to 6-membered carbon ring which contains 1, 2 or 3 double bonds;

and a stabilizing effective amount of a noble metal ion in an amount of up to about 1 g/kg of compound of the formula I.

2. The solution according to claim 1, wherein Y is hydrogen or $(C_1-C_8)$-alkyl.

3. The solution according to claim 1, wherein Y is hydrogen or methyl.

4. The solution according to claim 1, wherein R and $R^1$ independently of one another are hydrogen or halogen.

5. The solution according to claim 3, wherein R is chlorine and $R^1$ is hydrogen.

6. The solution according to claim 1, wherein the noble metal ion is ruthenium, rhodium, palladium, osmium, iridium, platinum, silver or gold.

7. The solution according to claim 5, wherein the noble metal ion is silver, gold or palladium.

8. The solution according to claim 1, wherein the noble metal ion is in an amount from about 0.01 mg to about 1 about g/kg of compound of the formula I.

9. The solution according to claim 7, wherein the noble metal ion is in an amount from about 10 mg to 200 mg/kg of compound of the formula I.

10. The solution according to claim 9, wherein the compound of formula I is present in amounts from about 0.5 to about 10% by weight, based on the total solution.

11. The solution according to claim 1, comprises 5-chloro-2-methylisothiazolin- 3-one and 2-methylisothiazolin-3-one in a ratio of 1 to 10:1.

12. The solution according to claim 10, comprises 5-chloro-2-methylisothiazolin- 3-one and 2-methylisothiazolin-3-one in a ratio of 2 to 4:1.

13. A microbicidal agent for use in industrial systems in which microorganisms can grow comprising the solution as claimed in claim 1, wherein said solution protects against microorganisms.

14. A microbicidal agent for use in industrial systems in which microorganisms can grow comprising the solution as claimed in claim 12, wherein said solution protects again microorganisms.

15. The solution as claimed in claim 1, further comprising soluble salts.

16. The solution as claimed in claim 12, further comprising at least one cation lithium, sodium, potassium, calcium, barium, aluminum, iron, manganese, nickel, cobalt, tin, or zinc-ions.

* * * * *